(12) United States Patent
Viovy et al.

(10) Patent No.: US 8,741,661 B2
(45) Date of Patent: Jun. 3, 2014

(54) METHODS AND DEVICES FOR SAMPLING FLOWABLE MATERIALS

(75) Inventors: Jean-Louis Viovy, Paris (FR); Max Chabert, Paris (FR)

(73) Assignees: Institut Curie, Paris (FR); Centre National de la Recherche Scientifique, Paris (FR)

(*) Notice: Subject to any disclaimer, the term of this patent is extended or adjusted under 35 U.S.C. 154(b) by 711 days.

(21) Appl. No.: 12/438,233

(22) PCT Filed: Sep. 12, 2007

(86) PCT No.: PCT/IB2007/053678
§ 371 (c)(1),
(2), (4) Date: May 22, 2009

(87) PCT Pub. No.: WO2008/032276
PCT Pub. Date: Mar. 20, 2008

(65) Prior Publication Data
US 2009/0288710 A1    Nov. 26, 2009

(30) Foreign Application Priority Data

Sep. 13, 2006    (EP) .................................. 06019153

(51) Int. Cl.
*G01N 1/16*    (2006.01)
*G01N 1/18*    (2006.01)

(52) U.S. Cl.
USPC ......................................... 436/180; 436/174

(58) Field of Classification Search
CPC ....................................................... G01N 1/16
USPC .............. 422/62, 68.1, 81, 82, 500, 501, 509, 422/510, 511, 514, 515, 516, 519, 520, 521, 422/522, 523; 436/43, 174, 180; 73/61.59, 73/64.56, 863, 863.01; 435/287.3
See application file for complete search history.

(56) References Cited

U.S. PATENT DOCUMENTS 4,678,641 A  *   7/1987   Cassaday ....................... 422/527
6,130,098 A      10/2000   Handique et al.
(Continued)

FOREIGN PATENT DOCUMENTS

EP     1 637 226 A1    3/2006
EP     1790966 A1  *   5/2007
(Continued)

OTHER PUBLICATIONS

Curcio et al., "Continuous Segmented-Flow Polymerase Chain Reaction for High-Throughput Miniaturized DNA Amplification," *Anal. Chem.*, vol. 75, No. 1, Jan. 1, 2003, pp. 1-7.

(Continued)

*Primary Examiner* — Christopher A Hixson
(74) *Attorney, Agent, or Firm* — Oliff PLC (57) ABSTRACT

A method including: a) providing a first well with a first layer of a first flowable material and a second layer of a second flowable material, and a second well with a first layer of a first flowable material different from the first flowable material of the first well, b) locating the flowable material inlet within the first layer, c) sampling a first volume of the first flowable material, d) displacing the flowable material inlet relative to the first well to locate the flowable material inlet within the second layer, e) sampling a second volume of the second flowable material, f) displacing the flowable material inlet relative to the first and second wells to locate the flowable material inlet within the first layer of the second well, and g) sampling or dispensing into the second well a third volume of the first flowable material of the second well.

36 Claims, 7 Drawing Sheets

(56) References Cited

U.S. PATENT DOCUMENTS

| | | | |
|---|---|---|---|
| 6,149,787 A * | 11/2000 | Chow et al. | 204/451 |
| 2002/0009392 A1 | 1/2002 | Wolk et al. | |
| 2006/0062696 A1 * | 3/2006 | Chow et al. | 422/100 |

FOREIGN PATENT DOCUMENTS

| | | |
|---|---|---|
| GB | 2 130 553 A | 6/1984 |
| WO | WO 98/33052 | 7/1998 |
| WO | WO 00/21666 A1 | 4/2000 |
| WO | WO 02/30561 A2 | 4/2002 |
| WO | WO 2005072858 A1 * | 8/2005 |

OTHER PUBLICATIONS

Litborn et al., "Liquid lid for biochemical reactions in chip-based nanovials," *Journal of Chromatography B.*, vol. 745, 2000, pp. 137-147.

Curcio, "Improved Techniques for High-Throughput Molecular Diagnostics," Ph.D. Thesis, *Royal Institute of Technology, Department of Chemistry, Division of Analytical Chemistry*, Stockholm, Sweden, 2002, pp. i-xii, 1-61 and annexes.

* cited by examiner

METHODS AND DEVICES FOR SAMPLING FLOWABLE MATERIALS

BACKGROUND

Further advances in the genomics revolution, most importantly applications to medicine and diagnosis, will require low-cost, user-friendly, high-throughput and accurate tools for analyzing biomolecules. At the present time, the most pressing need is to reduce the consumption of biological samples and reagents. The bottleneck is not detection, since current equipment can work into the nano- to pico-molar range with nanoliter volumes, but rather fluid manipulation and the problem of introducing conveniently the samples and reagents in the system.

Robots, pipettors and microtiter plates (MTP) systems are generally limited to volumes above a few microliters by surface tension and evaporation.

A simple, robust method for handling sub-microtiter sample and reagent volumes and interfacing them with the outside world would thus have a tremendous impact on a wide range of high-throughput bioanalytical processes.

In the Bioanalyzer® device commercialized by Agilent, the sample is pipetted into vials in the microfluidic chip with conventional manual pipettors. Thus samples volumes of several µl are required.

Conventional capillary electrophoresis apparatuses, presently commercialized by Applied Biosystems, Beckman, Agilent and the like, collect samples by dipping a capillary end into either microvials such as "Eppendorf tubes" or microtiter plates.

Known methods however can lead to some carryover of liquid, because a drop of liquid, representing a volume much larger than the volume of liquid introduced into the capillary, can hang onto the capillary tip, and be transported to another vial.

To minimize this carryover, protocols generally involve a washing step, in which the capillary tip is dipped into a wash liquid contained in a second vial, before the tip is dipped into a buffer vial or another sample.

Patent US2002009392 to Jeffrey et al. discloses a method that involves a relative motion of the capillary tip and the wash liquid, which allows a better cleaning than a simple dipping. This method, however, involves a relatively long manipulation time. Also, this method does not solve the problem of evaporation, and thus requires relatively important sample volumes.

Litborn et al. in J Chromatogr B Biomed Sci Appl. 2000 Aug. 4; 745(1): 137-47 discloses to cover samples by a liquid lid consisting in a non-miscible, volatile fluid to prevent evaporation.

Another problem associated with the sipping of samples into capillaries is that when the tip is removed from a sample vial, because of hydrostatic forces, capillary forces and time constant of pressure regulation systems, either air can be spuriously injected into the channel, generating unwanted distorsion of flow and numerous possible inconveniences, or some fluid from the hanging drop may continue to be injected into the capillary, leading to irreproducible volume sampling.

To address this problem, U.S. Pat. No. 6,149,787 to Chow et al. discloses a method of sampling fluid comprising:
- dipping an open end of an open ended capillary element comprising a capillary channel disposed therethrough, into a source of second fluid, the capillary channel being filled with a first fluid;
- withdrawing the capillary element from the second fluid; permitting an amount of the second fluid remaining on the open ended capillary to spontaneously inject into the capillary channel;
- dipping the capillary element into a third fluid after a first selected time period, the first selected time period being controlled to control the amount of the first fluid permitted to spontaneously inject into the open ended capillary channel.

This way, the quantity of sample introduced into the capillary is controlled thanks to the selected time period elapsed between dipping the capillary tip into the second fluid and into the third fluid. However, this method requires a precise control of the displacement of the tip, and it puts a lot of constraints on the injection process. For instance, if samples must be introduced from many different vials, such as in a microtiter plate, the injection time cannot be smaller than the time necessary for displacing the tip from the farthest vial to the buffer vial. Oppositely, if large samples must be injected, large waiting times must be used, which is detrimental to throughput.

Another difficulty in microcapillary and microfluidic systems is that transport of minute samples in thin capillaries leads to dispersion, cross contamination and dilution, due to the Poiseuille flow profile. A useful solution to this problem consists in transporting samples and reagents as droplets in an immiscible fluid.

Droplet systems, typically consisting of water droplets in oil or a fluorinated solvent, have received much attention in microfluidics as a method for producing precise emulsions, as discrete microreactors for polymerase chain reaction (PCR), for the measurement of fast kinetics, and for the dispersion-free transport and manipulation of sample aliquots.

Considerable efforts have thus been developed in the last years to create and/or manipulate microdroplets.

Some devices, such as disclosed in U.S. Pat. No. 6,130,098, for instance, use hydrophobic forces, by moving such droplets in microchannel combining some hydrophilic and some hydrophobic portions.

Manipulation of droplets on planar arrays of electrodes by electrowetting has also become very popular, since such manipulation allows one to address droplets to diverse locations and along complex and programmable paths.

Dielectrophoresis is another way of transporting and mixing droplets or solid objects such as cells or latex particles.

Transporting and mixing droplets in an elongated microchannel, or in a network of connected microchannels avoids evaporation and allows transport on long distances by simple hydrodynamic mobilization of a carrier fluid surrounding the droplets.

Droplets can thus be transported in capillaries several meters long, and used as microreactors, as disclosed e.g. in Curcio and Roeraade, Anal. Chem., 75, 1-7 (2003). When interaction with the walls is well controlled, all droplets move at the same velocity, and very stable trains are achieved, preventing unwanted mixing of neighboring droplets.

M. Curcio in *Improved Techniques for High-Trough put Molecular Diagnostics*, Ph. D. Thesis, discloses inter alia to serially inject reaction mixtures into a capillary tube as small plugs separated by a hydrophobic transport liquid to perform sequenced-flow PCR.

In some cases, however, it may be desirable to mix two droplets transported in a channel.

Patent application EP 04 2921734 to Viovy et al. provides a way to coalesce two droplets in a microchannel, using an electric field. This method, however, does not solve the world-to-chip interface, i.e. it does not provide a way to introduce the two reagents to be coalesced, in a way that would be both versatile, rapid, robust and convenient.

SUMMARY

The present invention aims to improve further the sampling and manipulation of fluid packets in microchannels.

The invention also aims to reduce cross contamination of sampled liquids while permitting quick sampling of various fluids.

A further aim of the present invention is to provide a solution for mixing if necessary at least two sampled liquids before performing a treatment or analysis of the mixture.

A first object of the invention is a method for manipulating, for example sampling, different fluid materials, for example flowable materials, with a microsampler head having at least one fluid inlet, said method comprising:

a) providing at least a first well with at least a first layer of a first fluid and a second layer of a second fluid immiscible with the first fluid, located over said first layer, and at least a second well with at least a first layer of a first fluid different from the first fluid of first well, b) locating the at least one fluid inlet of the microsampler head within the first layer of said first well, c) sampling into the microsampler head a first volume of the first fluid of the first well, d) displacing the at least one fluid inlet relative to the first well to locate the at least one fluid inlet within the second layer, e) sampling into the microsampler head a second volume of the second fluid, f) displacing the at least one fluid inlet relative to the first and second wells to locate the at least one fluid inlet within the first layer of the second well.

g) sampling into the microsampler head a third volume of the first fluid of the second well or delivering into said second well from the microsampler head a third volume of said first fluid from said first well.

The third volume of the first fluid may be equal to the first volume of the first fluid or may be less.

The first and third volumes may form primary droplets in a microchannel defined by the microsampler head.

Such a method allows manipulation, for example sampling, of two different fluids or more while limiting cross contamination.

By <<flowable material >> is considered in the invention any condensed matter amenable to irreversible changes of shape by applying a mechanical constraint. This involves in particular all common liquids, but it may also comprise, in some embodiments, e.g. pastes, liquid polymers, plastic hydrogels, or powders, but excludes gases and vacuum. In some exemplary embodiments in which long-term operation is required, at least some of the flowable materials used in the invention, and preferably all them, are non-volatile, or moderately volatile.

The second well may contain more than one fluid layer, for example as many fluid layers as the first well.

The second well may comprise over the first fluid a second layer of a second fluid immiscible with the first layer fluid and the second layers of the first and second wells may not be in fluid communication. This allows sampling of the second fluid and may limit cross-contamination.

This also prevents evaporation of water-based fluids or other first fluids and thus allows for the long-term conservation and repetitive sampling from minute volumes. The quantity of liquid sampled may be adjusted at will, by properly tuning sampling means used for sampling, e.g. the flow velocity or the pressure in the microsampler head depending if aspiration is performed in flow control or in pressure control mode, and the duration of sampling.

Exemplary embodiments of the invention are suitable for manipulating a large range of volumes, including the typical volumes manipulated with current fluid manipulation tools.

Exemplary embodiments of the invention allow to manipulate minute volumes, i.e. volumes impossible to manipulate with state of the art tools.

It allows, for instance the long-term and accurate manipulation of volumes less than 2 µl, for example less than 1 µl or less than 0.2 µl. Indeed, exemplary embodiments of the invention are advantageous for manipulating any fluid volumes in the nanoliter range, or even in the picoliter range.

The first well may further be provided with a third layer of a third fluid located over the second layer and immiscible with the second fluid.

The method may further comprise displacing the at least one fluid inlet relative to the first well after sampling the second volume of the second fluid in the first well to move the at least one fluid inlet from the second layer into the third layer of the first well. This enables washing of the microsampler head.

The second well may also be provided with a third layer which may consist of the same liquid as the third layer of the first well and the third layers of the first and second wells may be in fluid communication, thus allowing displacement of the at least one fluid inlet without contact with air.

The method may comprise displacing laterally the at least one fluid inlet within the third layer from over the first well to over the second well.

In this particular embodiment where the second well is also provided with a third layer and the third layers of the first and the second wells are in fluid communication, the method is particularly advantageous in terms of limitation of cross contamination and of long-term conservation and repetitive sampling from minute volumes.

Another advantage of this particular embodiment is that it allows all these samplings without ever having the microsampler head exposed in open, thus avoiding contamination and unwanted introduction of air, and minimizing uncontrolled introduction of liquid by capillary forces.

The second fluid of the first and second well may be the same fluid and may be used as a carrier fluid.

The method may comprise, after sampling into the microsampler head the third volume of the first fluid of the second well:

h) displacing the at least one fluid inlet relative to the second well to locate the at least one fluid inlet within the second layer of the second well, i) sampling into the microsampler head a fourth volume of the second fluid.

The fourth volume of the second fluid may be larger than the second volume to serve as a spacer during the displacement of a series of droplets. The second volume may be small enough not to prevent coalescing of the droplets made by the first and third volumes of the first fluids of respective first and second wells.

A further object of the present invention is a method for coalescing at least two primary droplets, which may contain liquid, $a_i$ and $a_j$ respectively, sampled into a microchannel, which may be part of the microsampler head defined above, said primary droplets being separated by a volume of an immiscible fluid serving as a carrier fluid or miscible with said carrier fluid, wherein said primary droplets are displaced from a first portion of the microchannel having a first cross-sectional area to a second portion of the microchannel having a second cross-sectional area larger than said first cross-sectional area, and wherein the resulting droplet has a prolate shape in said second portion of the microchannel. Thus, the resulting droplet should have a volume at least equal to $$\frac{4}{3\sqrt{\pi}}S^{3/2}$$

in circular channels or $$\frac{\pi}{6}S^{3/2}$$

in square channels, where S is the section of the second portion of the channel.

Such a method of coalescing droplets is easy to implement and allows efficient manipulation of the resulting droplet.

According to a specific embodiment, such a method further comprises coalescing primary droplets of fluids ($a_i$, $a_j$) originating from the first ($w_i$) and second wells ($w_j$).

Preferably, the microchannel's surface is wetting for the carrier fluid, and non-wetting for the two primary droplets. Some methods for obtaining desirable wetting properties are disclosed e.g. in EP 04 2921734 which is incorporated by reference. For instance, if the primary droplets are water-based, the carrier fluid may be a fluorocarbon, for instance FC40, 3M, which may be supplemented with 0.5 wt % of a fluoroalcohol surfactant (1H,1H,2H,2H-perfluorodecan-1-ol, Fluorochem) and the microchannel may comprise a Teflon® tubing.

Primary droplets may be arranged in series, and the primary droplets in a given series may be coalesced together, but the resulting droplet (also called secondary droplet) from the coalescence of one series may not be coalesced with any of the droplets resulting from the coalescence of primary droplets in other series.

The method involved a discontinuous flow in the microsampler head because the flow may be discontinued during displacement of the microsampler head between layers. For some operations imposed onto the fluid samples downstream of the microsampler head, however, it may be interesting to have a flow which is continuous and a further object of the present invention is a method for supplying an apparatus with fluid samples, which may enable to obtain a continuous flow. This method for supplying comprises:

thanks to first and second pumps, alternately drawing through a sample channel into first and second temporary storage channels droplets of samples in a carrier fluid, alternately pushing droplets of samples in the carrier fluid from the first and second buffer channels into an outlet channel, wherein when samples are drawn into the first buffer channel by the first pump samples are pushed by the second pump from the second buffer channel into the outlet channel and when samples are drawn into the second buffer channel by the second pump samples are pushed by the first pump from the first buffer channel into the outlet channel.

This enables to obtain a continuous flow.

A further object of the present invention is a sampling-containing structure comprising a plurality of wells, each well of the plurality comprising a first portion being hydrophobic and a second portion being hydrophilic, at least one of the first and second portions being made of thermoplastic material.

Preferably, the sample-containing structure is positioned during operation, in an orientation such as the two said portions are ordered vertically.

In a particular embodiment, the wells may be cylindrical or conical, a first portion of the length of the lateral wall of the cylinder (resp. cone) being hydrophobic and a second portion of that length being hydrophilic, at least one of the first and second portions being made of thermoplastic material As another specific embodiment, the wells may be cylindrical, the side wall of the cylinder being hydrophobic and the bottom face being hydrophilic.

In yet another embodiment, the wells may be cylindrical, the side wall of the cylinder being hydrophilic and the bottom face of the cylinder being hydrophobic.

Such a sampling structure is very convenient to help achieve the various arrangements of fluid layers used in implementing the method of sampling defined above.

A further object of the invention is a cover plate comprising:

an apertured support, a plurality of skirts each extending below a corresponding aperture of the support and suitable for being inserted into a corresponding well of a microtiter plate on which the cover plate is placed.

Such a cover plate may be useful to easily obtain wells with different wetting properties.

A further object of the invention is a microsampler head comprising:

a first microchannel portion defining at least one fluid inlet and having a first internal cross-sectional area $s_1$, a second microchannel portion in which the first microchannel portion opens out, the second microchannel portion having a second cross-sectional area $s_2$ larger than the first cross-sectional area, wherein $1 < s_2/s_1 \leq 100$, and preferably $2 < s_2/s_1 \leq 10$ and $s_2 \leq 10$ mm$^2$, and preferably $s_2 \leq 2$ mm$^2$.

A further object of the invention is a multiplicity of droplets sequentially arranged in a microchannel into several series of droplets, wherein:

each droplet is essentially coaxial with the microchannel, the shortest distance between two consecutive droplets in one series is never larger than a distance a, and the shortest distance along the microchannel's axis between any two droplets belonging to two different series is never smaller than a.x, with x at least equal to 2, and preferably at least equal to 3, and wherein at least two droplets in at least one of said series of droplets contain liquids $a_i$ and $a_j$ respectively sampled from two different wells $w_i$ and $w_j$ into said microchannel.

With the rules given above, and using simple geometric calculations, those skilled in the art will be able to determine ratios of channel dimensions suitable for the invention, for any channel geometry.

For instance, a is equal to $$\frac{2}{3\sqrt{\pi}}\frac{S_2^{3/2} - S_1^{3/2}}{S_1}$$

in circular channels and a is equal to $$(1-\pi/6)\frac{S_2^{3/2} - S_1^{3/2}}{S_1}$$

in square channels with first and second internal cross-sectional areas $S_1$ and $S_2$ respectively, and more precisely x is greater than $$\frac{2}{3\sqrt{\pi}} \frac{S_2^{3/2} - S_1^{3/2}}{S_1 \cdot a} \text{ in}$$

circular channels and x is greater than $$(1-\pi/6)\frac{S_2^{3/2} - S_1^{3/2}}{a \cdot S_1}$$

in square channel with first and second internal cross-sectional areas $S_1$ and $S_2$ respectively.

A further object the invention is a device for fluid sampling comprising a plurality of wells, the plurality comprising at least a first well ($W_i$) and a second well ($W_j$), each well ($W_n$) of the plurality comprising a first layer ($1_k$) of a first fluid ($a_k$) covered by a second layer ($2_k$) of a second fluid ($b_k$) immiscible with the first fluid and a third layer ($3_k$) of a third fluid (c) covering the second layer and immiscible with the second fluid, wherein the first ($W_i$) and second wells ($W_j$) have different first fluids ($a_i/a_j$) and the same third fluid (c) and wherein the third layers ($3_i/3_j$) of the first and second wells are in fluid communication.

The second fluid may be the same for the first and second wells and may serve as a carrier fluid.

The device may further comprise at least one microsampler head having at least one fluid inlet and a drive mechanism for displacing the at least one fluid inlet relative to the plurality of wells both vertically and horizontally.

The device may comprise an inlet and an outlet for renewing the third fluid and/or for controlling the temperature of the third fluid.

The device may comprise a temperature controller through which the third fluid flows to maintain the temperature of the third fluid at a selected value.

This may enable to achieve quick and precise control and/or monitoring of the temperature of the fluid layers in the wells.

DESCRIPTION

Wells and Fluid Layers

Figure 1:
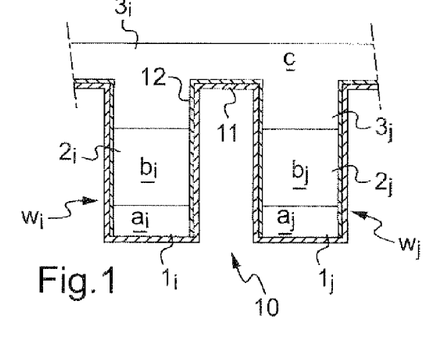
FIG. 1 is a schematic view of two wells filled with various fluids in accordance with the invention.

FIG. 1 shows two wells $w_i$ and $w_j$ which may belong to a same sampling structure 10.

The wells $w_k$ (where k is an integer ranging from 1 to the total number of wells) of the sampling structure 10 may have any volume, ranging from several ml to less than a nanoliter, depending on the intended use of the samples. The wells may have the same volume or not.

Figures 13, 14, 15, 16, 17:
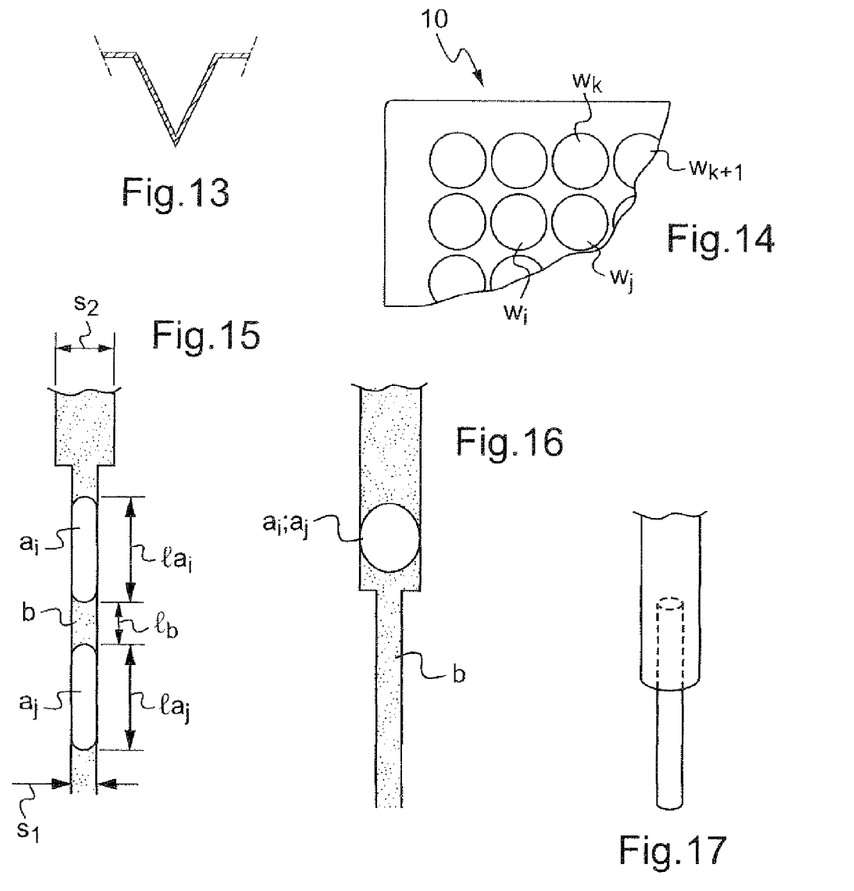
FIG. 14 is a plan a view of a sampling structure made in accordance with the present invention.
FIGS. 15 and 16 illustrate a method to coalesce droplets according to one aspect of the invention.
FIG. 17 is an elevation view showing a microsampler head.

In a preferred embodiment, the wells $w_k$ are organized in a regular array, as shown on FIG. 14.

According to one embodiment, the wells may be arranged in the device as an array compatible with the format of any of 48, 96, 384 or 1536-wells microtiter plates.

In an exemplary embodiment, the wells $w_k$ may belong to a microtiter plate 11 made of thermoplastic material.

A plurality of wells $w_k$ may each contain a respective first layer $1_k$ of a first fluid $a_k$ adjacent the bottom of the well $w_k$, a respective second layer $2_k$ of a second fluid $b_k$ over the first layer, the second fluid being immiscible with the first fluid $a_k$ and a respective third layer $3_k$ of a third fluid c which may be the same for all wells $w_k$ of said plurality.

In a variant (not shown) the different wells $w_k$ contain a third layer $c_k$ that is disconnected, i.e. does not entirely fill the wells.

In a preferred embodiment, the second layers $b_k$ of the different wells of the plurality are disconnected, i.e. they do not entirely fill each well. In another embodiment (not shown), the layers $b_k$ entirely cover at least some of the wells, thus providing a continuous fluidic communication between the second fluid layer of several wells.

The fluids $b_k$ may be the same fluid b, used as a carrier fluid.

In a variant, the second fluid ($b_i$) of the first well ($w_i$) comprises an organic solvent.

In a preferred embodiment, the fluid c (or a respective fluid $c_k$ in the non shown variant above) is miscible with any fluid $a_k$ (or the respective fluid $a_k$).

In a variant, the third liquid (c) of the first well ($w_i$) comprises water.

The fluids $a_k$ may correspond to different reagents and/or buffers, while the fluid c (or fluids $c_k$) may be a wash fluid.

The wash fluid may have any composition, depending on the contamination one wishes to avoid. It may contain, as a non-exhaustive and exemplary list, detergents, acids, bases, solvents, oxydants, or bactericides.

The first fluid $a_i$ of the first well $w_i$ may comprise water, the second fluid $b_i$ of the first well $w_i$ may comprise an organic solvent, and the third fluid may comprise water.

In a variant, the first fluid $a_i$ of the first well $w_i$ may comprise an organic solvent and the second fluid $b_i$ of the first well $w_i$ may comprise water and the third liquid c may comprise an organic solvent.

In another variant, the first fluid $a_i$ of the first well $w_i$ may comprise a non-fluorinated organic solvent or water and the second fluid $b_i$ of the first well $w_i$ may comprise a fluorinated solvent. Optionally, the third liquid c may comprise a non-fluorinated organic solvent, or water.

The first fluid $a_i$ may be less dense than the second fluid $b_i$.

The first fluid $a_i$ of the first well may comprise water and the first well $w_i$ may comprise a first portion having an hydrophilic surface in contact with the first layer $1_i$ of the first fluid $a_i$.

The first well $w_i$ may comprise a second portion having an hydrophobic surface.

In a preferred embodiment, fluid c (or fluids $c_k$) is less dense than fluid b (or fluids $b_k$).

Still in a preferred embodiment, fluid c (or fluids $c_k$) is a water-based solution, whereas fluid b (or fluids $b_k$) is a fluorocarbon liquid. In the latter case, if fluid $a_k$ is also water-based, and less dense than fluid $b_k$, the fluid $a_k$ can be kept at the bottom of the wells by treating the wells surface so that the bottom of the well is hydrophilic, whereas at least part of the wall of the well is hydrophobic.

Part of the wall of the well may be treated with a fluorinated material to obtain two portions having different wetting properties. In another variant, part of the well may be silanized.

There are various possibilities to obtain a well having at least one hydrophilic portion and at least one hydrophobic portion.

One possibility is to partially coat the surface of the well with a adhering coating not having the same wetting property as the material of the well.

For example, the microtiter plate may be made of a hydrophilic thermoplastic material and an hydrophobic coating 12 may be deposited along part of the length of the well, as shown in FIG. 1.

In a preferred embodiment, the second portion comprises a coating of a fluorocarbon material adhering to said thermoplastic material, or grafted onto it.

A convenient method for coating the wells is to fill the bottom of the wells with water and to spray a fluorocarbon resin such as Teflon® on the microtiter plate, as will be detailed further in the EXPERIMENTS section of the specification.

Figure 9:
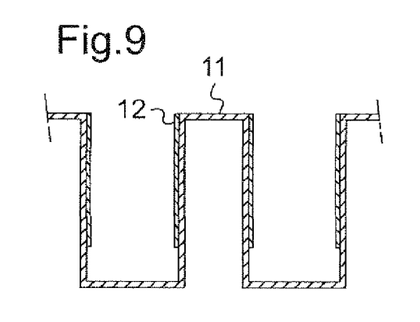
FIGS. 9 to 13 are various longitudinal cross sections of well embodiments.

The coating 12 may extend almost to the bottom of the well as shown in FIG. 1 or, depending the fluids to be hold in the wells, may end at a significant distance from the bottom, as shown in FIG. 9.

The coating 12 may or may not cover the walls connecting the wells.

Figure 10:
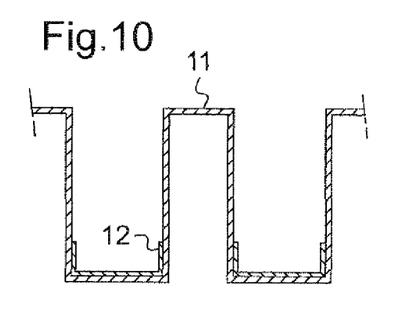

The coating 12 may extend also from the bottom and cover the latter, as shown in FIG. 10, and may end at some distance from the top of the well, the height of the coating 12 corresponding substantially for example to the height of the first layer $1_k$ or being higher.

Figure 11:
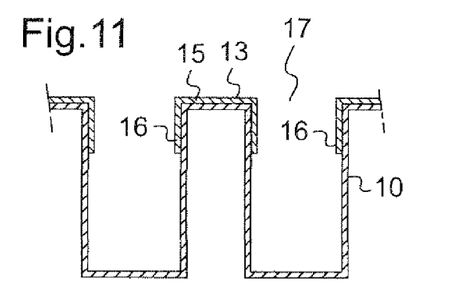

In a variant, the coating 12 is replaced by a cover plate 13 as shown in FIG. 11.

Such a cover plate 13 may comprise an apertured support 15 and tubular skirts 16 extending below each aperture 17 of the cover plate 15 into a corresponding well of the microtiter plate 10.

The cover plate 13 may be made of a thermoplastic material having a different wetting property than the microtiter plate 10, for example with an hydrophobic material in case the plate 10 is hydrophilic and vice versa.

Each skirt 16 may be force fitted into the corresponding well to obtain a sealed connection.

In another variant, each skirt 16 may have an outer diameter slightly smaller than the inner diameter of the hole in the titer plate it fits into, in order to be moved easily from one titer plate to the other.

In a variant not shown, the wells are coated in a lower portion and a cover plate is set on the microtiter plate.

This may enable to have three portions of the length of the well having different wetting properties.

Figure 12:
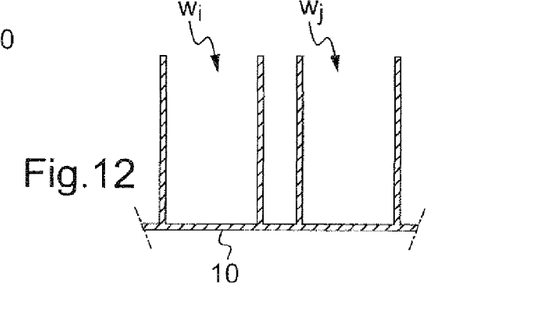

The wells may connect in various manner, at their upper end or bottom end, as shown in FIG. 12, or otherwise, for example thanks to a grid which may be manufactured separately from the wells.

The wells may also have a surface entirely hydrophilic or hydrophobic, depending of the nature of the fluids and their density.

The wells may have various shapes, for example a tapering shape as shown in FIG. 13.

The microtiter plate 11 may be held in a receptacle serving as a reservoir for the third fluid c, which may cover entirely the microtiter plate 11.

This receptacle may comprise a fluid inlet and a fluid outlet to enable renewal of the third fluid.

In a variant not shown, at least well $w_j$ contain only one liquid layer or only two liquid layer.

Method of Fluid Sampling

It is noticed that the invention is not limited to a specific embodiment of sampling. Any known method convenient for providing the microsampler with a volume of liquid may be used.

For example, the sampling method may be selected among passive sampling like a capillary sampling and an active sampling involving sipping under suction or overpression or an electric or magnetic field.

The method according to the present invention may also use a combination of previous specific sampling methods.

For example, sampling at step c) may comprise a depression within the at least one fluid inlet, as compared with the pressure at the top of said first ($1_i$) layer.

An embodiment of this method will be described in reference to FIGS. 2 to 8.

These figures show only two wells $w_i$ and $w_j$ but the method may be repeated with a larger number of wells, for example over ten.

Two consecutive samplings of fluids may occur in wells that are adjacent or not adjacent.

One well may contain a liquid that is to be mixed with a plurality of the first fluid of the first layer of different wells.

The method may start by sampling fluid $a_i$ in well $w_i$, with a microsampler head 20 having at least one fluid inlet 21.

Figure 2:
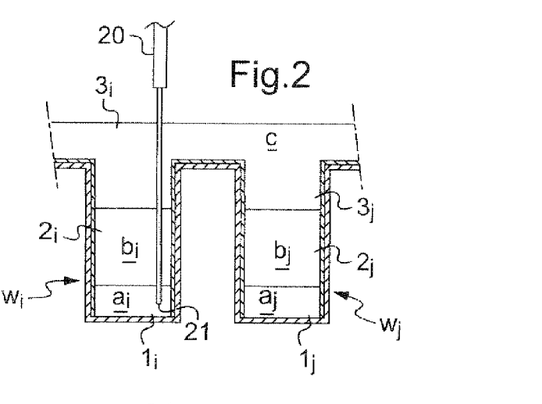
FIGS. 2 to 8 illustrate various steps of a method in accordance with the invention.

The microsampler head 10 is dipped in well $w_i$ across the fluid layers c and $b_i$, as shown in FIG. 2.

A volume of liquid $a_i$ may be sipped into the microsampler head for example thanks to suction created by a pump or by over pressure applied over fluid c.

Figure 3:
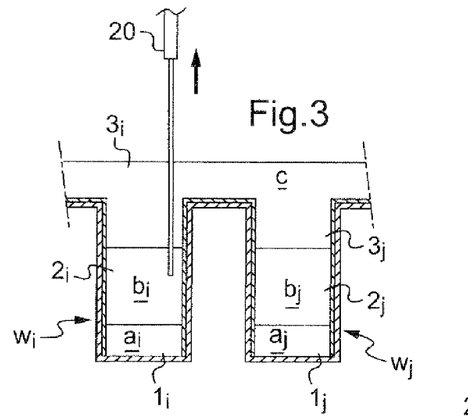

The microsampler head 20 is then raised and temporarily located in the second layer of fluid $b_i$ as shown in FIG. 3, to allow sampling into the microsampler head of a volume of carrier fluid $b_i$.

This sampling may result from capillary forces only, with no suction applied. In another variant, the sampling may result form suction applied by a pump or from over pressure applied over fluid c.

Figure 4:
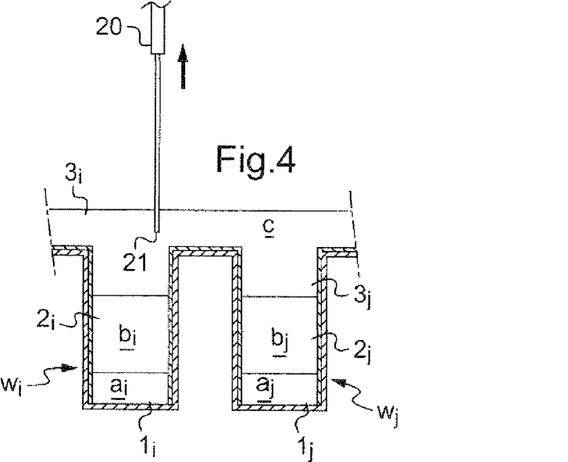

The microsampler head 20 may further be raised so that its head is located in the layer of wash fluid c, as shown in FIG. 4.

Figure 5:
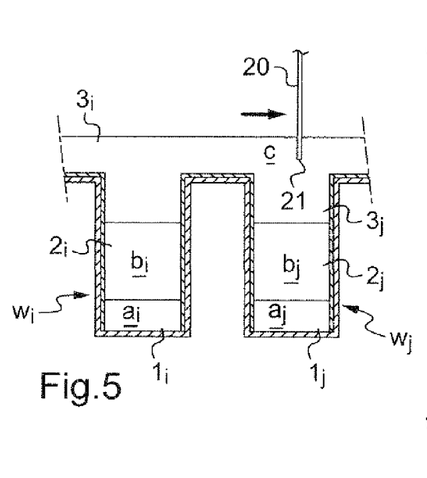

The microsampler may then be moved horizontally in the fluid layer c, as shown in FIG. 5, to be located over the second well $w_j$.

Figure 6:
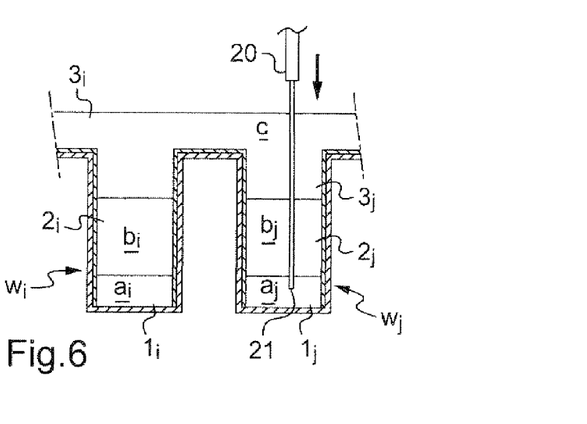

Then the microsampler head 20 may be lowered to sip a volume of the first fluid $a_j$ of well $w_j$, as shown in FIG. 6.

Figure 7:
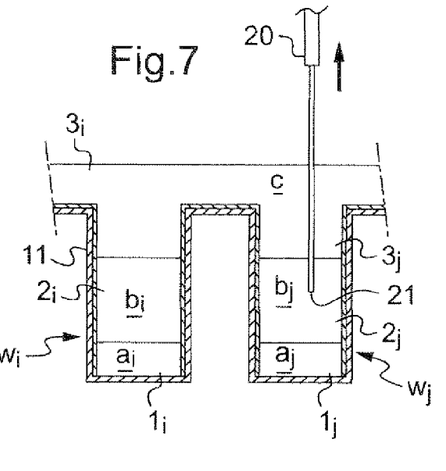
Figure 8:
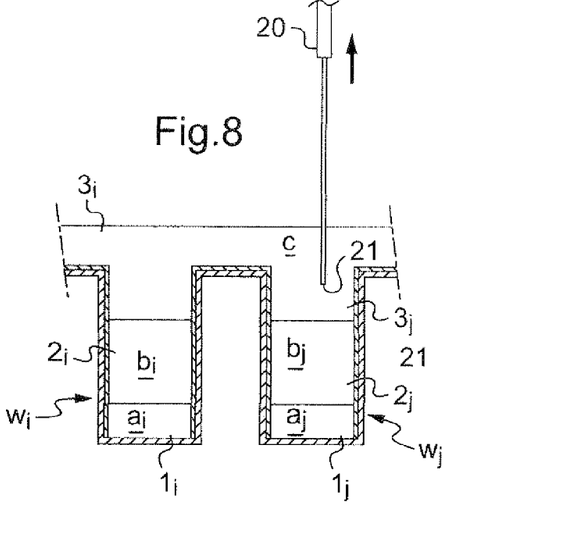

A volume of carrier fluid $b_j$ which is advantageously the same as fluid $b_i$ may then be sampled, as shown in FIG. 7.

This sampling may occur thanks to capillary forces or thanks to suction applied to the microsampler head or to overpressure applied over the fluid c, depending the volume of carried fluid $b_j$ one wants to sip.

Then the microsampler head may be raised again in the fluid c and displaced over another well.

Optionally, the layer of washing fluid c can be continuously renewed by a circulation system, if contamination is particularly critical.

The temperature of fluid c may be controlled during renewal or recirculation of the fluid.

In a specific embodiment, the sampling is performed from more than 10 different wells.

Method of Fluid Aliquoting

In another exemplary embodiment, the method of the invention may be used for aliquoting a primary fluid contained in a first well, or a selection of several primary fluids contained in a selection of first wells, as multiple aliquots each contained in a different second wells.

For instance, as referred with FIG. 2, this aliquoting can be achieved by first dipping the microsampler head 10 in well $w_i$ across the fluid layers c and $b_i$, as shown in FIG. 2.

A volume of liquid $a_i$ may be sipped into the microsampler head for example thanks to suction created by a pump or by over pressure applied over fluid c.

The microsampler head 20 is then raised and temporarily located in the second layer of fluid $b_i$ as shown in FIG. 3, to allow sampling into the microsampler head of a volume of carrier fluid $b_i$.

This sampling may result from capillary forces only, with no suction applied. In another variant, the sampling may result form suction applied by a pump or from over pressure applied over fluid c.

Optionally, the microsampler head 20 may further be raised so that its head is located in the layer of wash fluid c, as shown in FIG. 4.

The microsampler may then be moved horizontally in the fluid layer c, as shown in FIG. 5, to be located over the second well $w_j$.

Then the microsampler head 20 may be lowered into well $w_j$, and a volume of the first liquid $a_i$ be delivered into well $w_j$, using the same fluid displacement means as used for sampling from well $w_i$, acting in the opposite direction.

Preferably, the volume of liquid $a_i$ delivered in well $w_j$ may be equal to the first volume initially sampled from well $w_i$, but in some embodiments it may also be smaller.

In a first preferred embodiment, the well $w_j$ may already contain a first layer of a liquid $a_j$ miscible with liquid $a_i$, as shown in FIG. 6. In this embodiment, the aliquoting step leads to a direct mixing of liquids $a_i$ and $a_j$.

In another preferred embodiment (not shown), the well $w_j$ may only contain a first layer of fluid $b_j$, immiscible with liquid $a_i$ (and optionally a second layer of fluid c). This embodiment is preferred when aliquoting is needed but mixing with a second fluid is not required.

It will be obvious from those skilled in the art that operations of sampling, aliquoting and mixing can be combined at will in arbitrary orders, suitable for a given application.

The invention may thus provide a flexible, fully programmable platform for performing complex sample manipulation protocols without numerous limitations of prior art, such as evaporation, contamination by aerosols, and irreproducibility in the sampling of small volumes.

Microsampler Head

The microsampler head 20 may be made of any material and may be of any shape.

The opening 21 may be at the tip of the sampling head as shown or at its side (not shown).

Preferably the microsampler's surface is made of a material wetting for liquid $b_k$, and non-wetting for liquid $a_k$. This way contamination and volume incertitude are minimized.

The microsampler head comprises a first microchannel portion having a first cross-sectional area and a second microchannel portion having a second cross-sectional area larger that the first cross-sectional area, and wherein the coalescing occurs when entering the second microchannel portion.

Thus, the sampling device may comprise along its length, at some distance from the opening, a microchannel having an enlarged section as shown in FIG. 15. The section may change from a cross section $s_1$ to a cross section $s_2$, significantly larger than $s_2$. Preferably, $s_2$ is at least twice $s_1$, and more preferably at least four times $s_1$.

This configuration allows for a particularly simple and rapid online mixing of consecutive droplets by coalescence.

The enlarged section may be located within the microsampler head, the first microchannel portion being defined by a first duct force fitted into a second duct defining the second microchannel portion.

The cross sections $s_1$ and $s_2$ may be circular or have a different shape.

The cross sections $s_1$ and $s_2$ may be selected so as to enable coalescing of droplets by the method below.

Method of Coalescing Droplets

This method may comprise introducing a first liquid element to a first microchannel portion with a cross section $s_1$, in the form of a primary droplet with a cross section comparable to that of the first portion of the microchannel, introducing in said first microchannel portion a spacer of a carrier fluid, introducing a second liquid element in the first microchannel portion in the form of a primary droplet with a cross section comparable to that of the first portion of the microchannel, the carrier fluid being immiscible with said first and second liquid elements, moving said first fluid element, said spacer of carrier fluid and said second fluid element to a second portion of the microchannel with a cross section $s_2$ larger than $s_1$, as shown in FIGS. 15 and 16.

This method may occur on the microsampler head, the primary droplets containing fluids $a_i$ and $a_j$ respectively and the spacer comprising fluid $b_i$.

The volume $V_1$ of the first fluid element and the volume $V_2$ of the second fluid element may be selected to that these fluid elements, isolated in the second portion of the microchannel with cross section $s_2$, would occupy the whole cross section of the channel if they were not to coalesce i.e. for instance $$V_i > \frac{4}{3\sqrt{\pi}} s_2^{3/2} \qquad \text{(Equation 1)}$$

in a circular channel or $$V_i > \frac{\pi}{6} \cdot s_2^{3/2} \qquad \text{(Equation 2)}$$

in a square channel). The volume of the carrier fluid spacer $V_s$ may be selected so that the spacer, isolated in the second portion of the microchannel with cross section $s_2$, would not occupy the whole cross section of this channel (i.e. for instance $$V_s < \frac{2}{3\sqrt{\pi}} s_2^{3/2} \qquad \text{(Equation 3)}$$

in a circular channel or $$V_s < \left(1 - \frac{\pi}{6}\right) \cdot S_2^{3/2} \quad \text{(Equation 4)}$$

in a square channel.

The resulting droplet has a prolate shape.

In a preferred embodiment, the length $l_b$ of the carrier fluid spacer, along the microchannel's axis, is smaller than the length of the first fluid element $l_{ai}$ and the length of the second fluid element $l_{aj}$, as shown in FIG. 15.

Series of Droplets

Figures 20, 21:
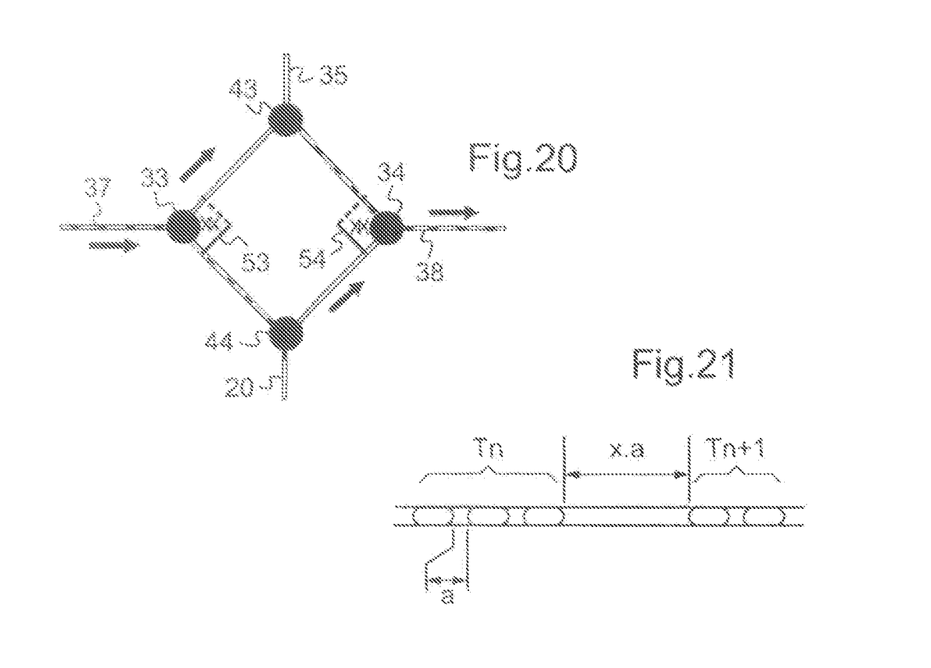
FIG. 20 illustrates the operation of the device of FIG. 19.
FIG. 21 shows a multiplicity of droplets.

The method of coalescing may be used to mix more than two droplets, for example 3, 4, 5 or more. In that case, the droplets to be mixed may be arranged in a "series" $T_n$ and $T_{n+1}$ of droplets as shown in FIG. 21, each droplet being separated from the previous one or the next one in the series by a carrier fluid spacer.

The spacer of carrier fluid separating two series of droplets may be large enough not to allow for the coalescence of two droplets from different series.

The shortest distance between two consecutive droplets in one series $T_n$ may never be larger than a distance a, and the shortest distance between any two droplets belonging to two different series $T_n$ and $T_{n+1}$ may never be smaller than a.x, with x at least equal to 2. Preferably, x is equal to 3, and more preferably to 5. More detailed formulas for specific microchannel shapes, such as Equations 1 to 4 above, can be used.

Preferably, at least two droplets in a series may contain different liquid sampled from different wells. The series may be pairs of droplets, each containing two droplets only.

For instance, a first droplet in a series may contain a first liquid, and the second droplet in the series may contain a first reagent able to react with a compound in the liquid.

The first droplet in a second series may contain a different liquid, and the second droplet in the second series may contain either the same first reagent, or a second reagent, able to react with said second liquid. By suitably sampling liquid elements from different wells (or other vials) as droplet series, it may be possible to automate complex combinations of reactions with libraries of samples and reagents, in a manner much more convenient than in the prior art.

The series $T_n$ and $T_{n+1}$ may be present in the microsampler head 20 only.

Device for Sampling Fluids

Figure 18:
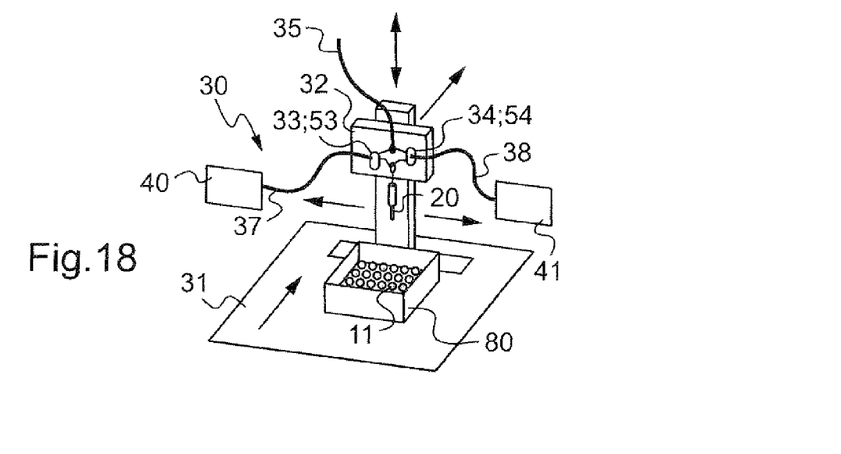
FIGS. 18 and 19 show a device for fluid sampling made in accordance with the invention.

FIG. 18 shows a device 30 for sampling fluids that may be used in association with the sampling structure 10 described above.

The device 30 may comprise a base plate 31 on which a receptacle 80 holding the microtiter plate may be located, as shown.

Figure 19:
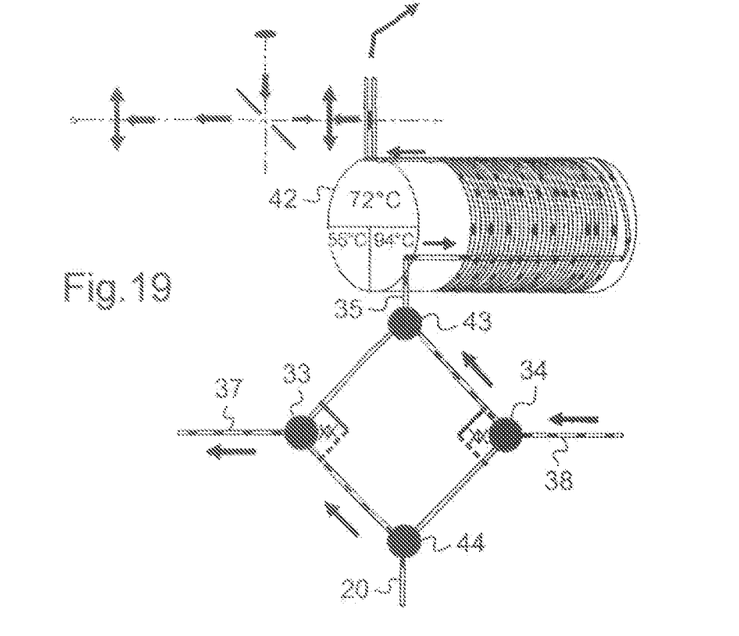

The device 30 also comprises a 3-axle motorised support 32 (also called robot) carrying at least the microsampler head 20 and which may also carry a fluidic system for connecting the microsampler 20 to pumps 40 and 41 and to an analyser shown in FIG. 19.

The motors of the support 32 may be controlled by a computer (not shown) operating a software for controlling adequate displacement of the microsampler head and operation of pumps and of the fluidic system.

This fluidic system may comprise electro pinch valves 53 and 54 and various fluid Y connectors 33, 34, 43 and 44, for example those described later in more details in the EXPERIMENTS section of the specification. In preferred embodiments, the valves may be pinched valves, and may be controlled by a computer The Y connector 43 is connected to an outlet channel 35 and to the Y connector 33 associated to the pinch valves 53 and to the Y connector 34 associated to the pinch valve 54 while the Y connector 44 is connected to the microsamples head 20 and to the Y connectors pinch valves 33 and 34.

The Y connectors 33 and 34 are connected via first and second buffer channels 37 and 38 to the pumps 40 and 41 respectively, which may be syringe pumps.

The computer may control operation of pumps and valves so that the first and second pumps alternately draw through the microsampler head into first and second buffer channels 37 and 38 droplets of samples in the carrier fluid and alternately push droplets of samples in the carrier fluid from the first and second buffer channels into the outlet channel 35.

When samples are drawn into the first buffer channel 37 by the first pump 40 samples are pushed by the second pump 41 from the second buffer channel 38 into the outlet channel 35 as shown in FIG. 19. When samples are drawn into the second buffer channel 38 by the second pump 41 samples are pushed by the first pump 40 from the first buffer channel 37 into the outlet channel 35 as shown in FIG. 20.

This enables continuous flow through the outlet channel into a device for fluid analysis or treatment, 42. In a preferred embodiment, presented in FIG. 19, the device is a DNA analysis device, and more specifically a device allowing Polymerase Chain Reaction by circulating samples sequentially around cylinder sections at different temperatures. However, in other preferred embodiments, the device connected to the outlet channel can be any kind of device able to perform the sampling, treatment, analysis, storage, or transport of fluids.

Applications

The invention may have many applications, for example in:
- automation of all operations requiring the mixing of at least two reagents, especially in small volume, and for high throughput,
- analysis and/or characterization of DNA, proteins, cells, organelles, polysaccharides, small molecules, polymers, oligomers, latexes, ions, etc. . . . ,
- combinatorial chemistry,
- amplification of nucleic acids by PCR, RCA, NASBA, isothermal amplification,
- protein treatment, digestion,
- electrophoresis,
- lab-on-chip, point of care devices,
- preparation of emulsions, latexes, liposomes, molecules, nanoparticles, microparticles, quantum dots, polymers,
- drug discovery,
- search for GMO, bacteria, viruses, pathogen compounds or organisms, forensic analysis, genotyping,
- studies of genome, transcriptome, proteome, of organisms or cells,
- search for drugs, pollutants,
- screening of the toxicity and or efficiency of potential drugs.

The invention thus has for object a method for performing one of these applications thanks to any methods and devices defined above.

Experiments

Non limitative experiments are disclosed hereunder for PCR analysis, for demonstrating some results obtainable thanks to various aspects of the invention.

Carrier Fluid.

The carrier fluid b in all experiments is perfluorinated oil (FC40, 3M) supplemented with 0.5 wt % of a fluoroalcohol surfactant (1H,1H,2H,2H-perfluorodecan-1-ol, Fluorochem). The surfactant is dissolved in the carrier fluid FC-40 by shaking the solution overnight. Before use, the oil is degassed under vacuum for at least 20 minutes.

MTP Surface Treatment.

Starting from a hydrophilic microtiter plate (Nunc Multisorp), the bottoms of the wells are covered with a thin layer of distilled water, and Teflon® is vaporized on the whole plate using a Teflon® spray (Roth). The plate is then dried at ambient temperature for 2 hours, the water is removed from the bottom of the wells, and the plate is carefully rinsed with distilled water. The plate is then dried again at ambient temperature overnight, yielding wells with a hydrophilic bottom and highly hydrophobic vertical walls. The prepared plates (hereafter called PMTP, Prepared MicroTiter Plates) may be washed with distilled water and detergents and reused at least 100 times before observable degradation of the surface treatment, although for routine operation a disposable PMTP is probably preferable.

MTP Preparation.

Aqueous samples a are placed at the bottom of the wells of the PMTP, and covered with a thick (200 µl in 96-wells PMTPs) layer of carrier fluid b. The covering prevents evaporation, isolates the samples from the reagents and the wash layer c, and acts as a reservoir of carrier fluid.

As commercial enzyme mixes are formulated with stabilizing surfactants, enzyme wells may be covered with surfactant free perfluorohexane instead of carrier fluid. Perfluorohexane is less dense than FC40, ensuring the stability of the enzyme wells even though the surface tension effect is weaker than in the sample wells.

Fluid Circulation Control

The simultaneous preparation of new samples and circulation in the PCR capillary is made possible with the device shown in FIGS. 18 and 19.

The tubing (buffer channels 37 and 38 and similar channels) may for example be 760 µm i.d. Teflon® PFA (Fisher Bioblock). Y-connectors 43 and 44 are in Teflon® (800 µm i.d., Omnifit).

The syringe pumps 40 and 41 are from Harvard Apparatus, equipped with Hamilton 250 µL syringes. The pinch valves 33 and 34 are electrovalves from NSresearch.

The pinch valves may operate with flexible silicone tubing (760 µm i.d., Fisher-Bioblock). To avoid contamination of the droplets by interaction with the walls and ensure the stability of the droplet train, the silicone tubing may be fluorosilanized as described below.

Silicone Tubing Silanization.

Pieces of silicone tubing (2.5 cm, 760 µm i.d., 2.4 mm o.d.) were cut, thinned, and placed in the pinch valves. Surface treatment was done automatically "on-line" using the fluid control software. The silicone surface was activated by circulating 1M hydrochloric acid at 1 mm/s in the whole injection system for one hour. HCl activation proved efficient on this commercial tubing. The tubing was dried by nitrogen flushing and rinsed by circulating methanol at 1 mm/s for 15 minutes. The tubing was dried again by nitrogen flushing, and a 5% wt. solution of 1H,1H,2H,2H-perfluorodecyltriethoxysilane (Fluorochem) in methanol was circulated at 1 mm/s for 2 hours in the fluidic system. The whole system was again carefully rinsed with methanol for 1 hour. The obtained coating was robust, may be "renewed" using the same protocol without changing the tubing.

Operation

One pump worked to sequentially form pairs of 500 nL primary droplets, one from the PCR mix and one from a sample well, separated by a thin perfluorohexane film taken up by capillarity as the tip moves through the enzyme well oil covering.

Different PCR mixes and samples were loaded in the same PMTP (or, with straightforward modification of the robotics, two PMTP may be managed simultaneously) and the system provided total freedom for combining any mix with any sample. Pairs of droplets were separated from each other by a 5 µL plug of carrier fluid aspirated from the second fluid layers. Pairs of droplets coalesced in the tube enlargement region of the microsampler head 20, yielding resulting droplets that could not merge. The negligible volume of perfluorohexane separating two primary droplets easily mixed with the carrier fluid.

In parallel with this loading operation, the pinch valve of the other pump was opened towards the heating cylinder, and this pump pushed in a continuous mode the previously formed train of resulting droplets in free oil to maintain a continuous flow in the PCR region.

Precise synchronization between the pumps by a software written in Labview (National Instruments) allowed their functions to be switched once the aspirating pump has formed a new droplet train, to allow for amplification of the latter.

In the present implementation, for timing reasons one pump could form up to 19 droplets during one cycle, but this parameter may vary over a large range depending on the internal diameter of the Teflon® capillary and on the chosen timing of the PCR cycles.

For each experiment, the first drop passing through one part of the system (i.e. the leading and trailing drop of each first series on a pump side) produced a distorted fluorescence signal to dust or impurities from the environment. Thus one started and ended the two first droplet-trains by dummy droplets containing PCR mix and no template. It is worth to note that with this simple precaution, in no case could contamination in any droplet was observed except the dummy ones, even when working with human DNA primers and low concentration templates, showing the robustness of this droplet microfluidics approach.

Temperature PCR Control

Briefly, a 4 cm diameter copper cylinder is divided in three temperature zones, one zone being twice as large as the other two. Each zone is insulated from its neighbors by low thermal conductivity polycarbonate sheets, and its temperature is precisely fixed using two Pt-100 thermocouples and a heating cartridge connected to a Keithley 2701 multimeter. The temperature in each zone is controlled by a custom PID controller written in Labview and interfaced via a pair of 7706 multiplexer cards. The capillary coil is surrounded by a first layer of aluminum foil in thermal contact with the regulated copper cylinder, in order to improve temperature uniformity across the capillary, and a second layer of thermal insulator. Air blown through bores drilled through the copper cylinder by a mini-turbine serves as a heat sink to shorten the thermal response time. The temperature uniformity in each sector was ±1° C. longitudinally, and the temporal stability was ±0.2° C., as measured by multiple scanning PT100 miniaturized sensors.

Optical Detection.

A 40 mW, 472 nm diode pumped solid state laser (AOTK) is reflected at 90° by a dichroïc mirror and focused on the Teflon capillary through a 10× microscope objective. The fluorescence is collected through the same objective and dichroïc mirror, then passes through a 510-550 nm bandpass filter (Thorlabs) and is focused by a converging lens on a photomultiplier (Oriel) equipped with a pinhole. The signal is acquired after amplification using the analog input of a PCI-6032E card (National Instruments) and recorded in Labview.

Data Treatment

Figure 22:
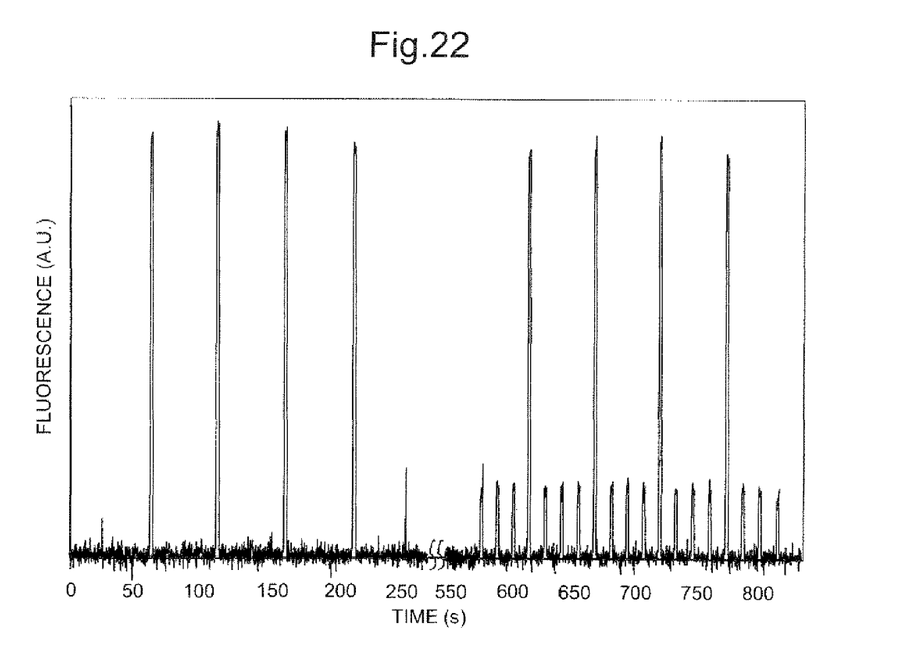
FIGS. 22 to 26 show results from experiments.

The data are collected with an average 150 ms period (50 ms mean deviation), and smoothed by a sliding 5 point summation. Blank droplets lead to a nonzero signal, because of the residual fluorescence of the dye (Sybrgreen or FRET reporters, depending on the fluorescence system chosen for quantification), and of possible interaction of the dyes with the primers. This origin of the non-zero signal is confirmed by two experimental observations:

(i) When tests are performed with enzyme and no primers in the common well, and sample wells containing either pure water or DNA template with primers, the water drops produce no fluorescence signal (see FIG. 22);

(ii) When water with mix and primers submitted to equivalent PCR cycles in a classical thermal cycler and subsequently spiked as drops into our detector, a fluorescence level comparable with that obtained with amplification in our flow through cylinder is observed, although it is not detectable on an agarose gel (see FIG. 23).

Calculated standard deviations on raw signal points were 2% for amplification of a sample initially containing 0.25 ng/µl template, and 15% for blank droplets, the latter being mainly linked to the detector background noise. The peak width, representing the passage time of one droplet, was also very uniform, with a standard deviation of 6%, independent of the presence or absence of template in the droplet.

To evaluate the quantity of amplified DNA, the total integrated peak area per drop was used: each raw signal peak is integrated by the Gauss method on a centered 25 data point interval, the results of this integration being divided by the corresponding time interval. The blank droplets amplitude distribution histogram presents a standard deviation of 5% (see FIG. 24). Thanks to this small fluctuation level, an average over a few droplets is sufficient to yield accurate baseline, standard deviation and 99% confidence interval (derived from the standard deviation assuming a classical Gaussian shape).

Biological Material.

The template DNA used in contamination, reproducibility and limit of detection experiments is a 2823 base pair DNA fragment of Litmus 28i (New England Biolabs) amplified on 572 base pairs from base 2008 to base 2580 (lower primer 5'-CGC-ATT-GCG-GTA-TCT-AGA-ACC-GGT-GAC-GTC-3', upper primer 5'-AGC-TTG-GAG-CGA-ACG-ACC-3', Eurogentech Oligold). The mix used for amplification is Sybr Green Jumpstart Taq Ready mix for quantitative PCR (Sigma), allowing fluorescence detection of the amplified products.

Clinical Samples

Clinical samples were extracted from human breast cancer cell lines T47D using the RNA plus kit (Bioprobe) according to the manufacturer instructions, and the quantity of RNA was measured by spectrophotometry at 260 nm. cDNA was synthesized by random-hexamer total RNA reverse transcription. 1 µg total RNA was reverse transcribed in 20 µL of 1× reverse transcriptase buffer (500 mM of each deoxynucleotide triphosphate, 3 mM $MgCl_2$, 75 mM KCl and 50 mM Tris-HCl, pH=8.3) with 10 units RNase inhibitor (Promega), 50 units Superscript II RNase H-reverse transcriptase (Invitrogen) and 1.5 mM random hexamer (Pharmacia). Samples were incubated at 20° C. for 10 minutes and 42° C. for 30 minutes, reverse transcriptase was then inactivated by heating at 99° C. for 10 minutes and cooling for 5 minutes.

Primers and probes were selected by Primer Express (Applied Biosystems) as previously described. For PR we used upper primer (SEQ ID NO 1) GAACCAGATGTGATCTAT-GCAGGA, lower primer (SEQ ID NO 2) CGAAAACCTG-GCAATGATTTAGAC and a 50-fold final dilution of the reverse transcribed DNA solution. For RPLPO, we used upper primer (SEQ ID NO 3) GGCGACCTGGAAGTC-CAACT, lower primer (SEQ ID NO 4) CCATCAGCACCA-CAGCCTTC, probe (SEQ ID NO 5) ATCTGCTGCATCT-GCTTGGAGCCCA and a 25-fold final dilution of the reverse transcribed DNA solution.

Results

FIG. 22 shows raw signal for 38 drops (two consecutive trains). The common well contained PCR mix without primers. In the first series, sample wells contained either pure distilled water or DNA at 0.5 ng/µL with primers (50 nM). Only the drops containing DNA and primers were detected (4 peaks, each separated by 3 undetectable water drops). In the second series, all drops contained DNA at 0.5 ng/µL, but only four of them (large peaks) also contained primers at 50 nM. Drops containing non-amplified DNA showed a small peak corresponding to Sybr green surface binding on DNA, as would be the case in a conventional thermocycler.

Figure 23:
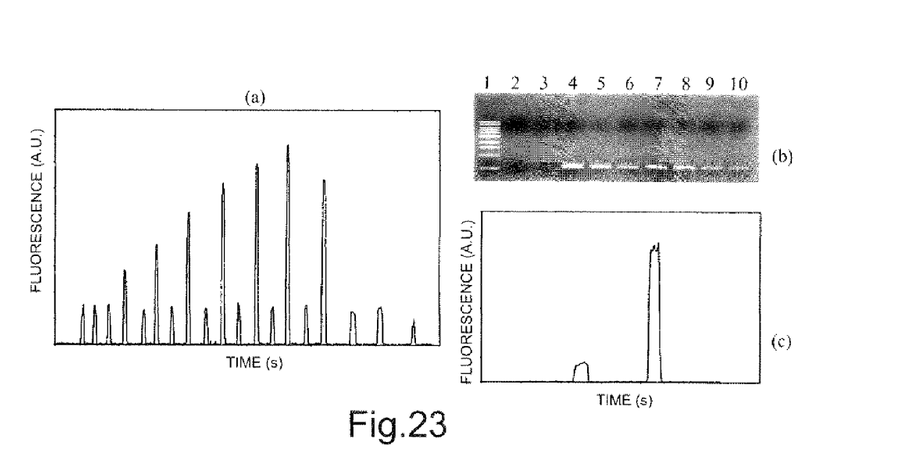

FIG. 23 shows (a) Amplification of increasing DNA concentrations after automatic injection and running of the samples in the automated system. Data points are acquired about every 100 ms from the photomultiplier and averaged on 5 points to level background noise. After 3 trailing and ending drops without template DNA, one drop with template DNA drop alternates with one drop without template DNA (to check for the absence of drop-to-drop contamination), and the DNA initial concentration is doubled every DNA drop. Fluorescence peaks corresponds to the band obtained on gel. The sixteenth droplet, which should show the highest fluorescence signal, actually has a lower signal than the former one, which may be caused by a fluorescence saturation effect. (b) Agarose gel of the equivalent amplification, performed in a conventional thermocycler and analyzed by gel electrophoresis: After automated injection of sample droplets, a 5 µL aliquot was pipetted from the common well, and either 5 µL of water or 5 µL of a DNA sample remaining in another well was added to this mix. The resulting mixture was cycled in a thermal cycler using the same protocol as in our system (94° C. for 30 s, 55° C. for 30 s and 72° C. for 1 minute), and the total mixture (10 µL) underwent electrophoresis on agarose gel. Lane 1, 1 kbp DNA ladder; Lane 2: common well mix with water taken from a milliQ machine; Lane 3: common well mix with water taken in one water well after automated drop injection; Lanes 4 to 10: common well mix with DNA samples of decreasing DNA concentration, corresponding to the large peaks in (a). No DNA is detected for water samples run in the classical cycler (lanes 2 and 3), confirming the absence of contamination in the mix and in the sample wells. The intensity of the DNA products in lanes 4-10 correlate with the intensities from the automated PCR machine. (c) Fluorescence curve obtained in the detector when manually injecting drops from amplifications run in the classical cycler: one drop initially containing water with mix (no amplification detectable on gel, lane 2) is followed by one drop initially containing DNA with mix (lane 4 on gel). The signal processing is identical to (b). The relative intensities of these peaks are identical to those observed in (a) during the normal use of the system.

Figure 24:
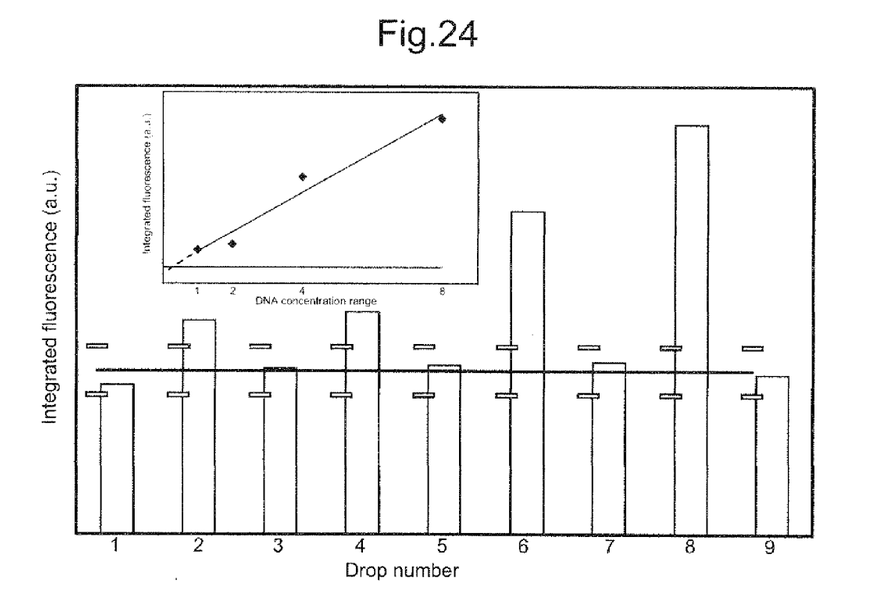

For the results shown in FIG. 24 the common well contains Sybrgreen premix with 50 nM primers. One control drop without template was injected between each DNA drop to control the absence of contamination between neighboring drops. The first amplified drop (peak number 2) initially contains 50 000 DNA molecules, and the concentration is doubled for each subsequent positive drop. Data are given as a histogram of integrated fluorescence intensities for each drop. First and last dummy drops are not shown. Dashed lines correspond to the average and 99% confidence interval, respectively, for blank drops (calculated on the integrated intensity). The inset shows integrated fluorescence intensity in positive drops as a function of their initial DNA concentration. The main line shows linear interpolation ($R^2$=0.9631). The bottom line shows the upper limit of the 99% confidence interval.

Figure 25:
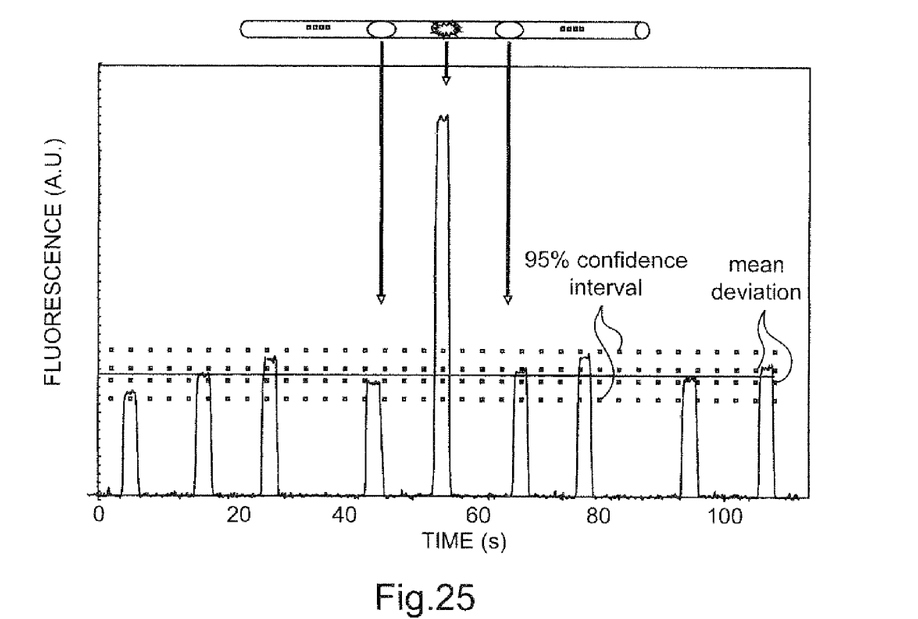

FIG. 25 shows fluorescence detection of the PR gene. The sample well contained a 25-fold dilution of material extracted from a cancer cell line T47d by total RNA extraction followed by reverse transcription from a 50 ng/µL total RNA solution. The common well contained Sybr Green Jumpstart Taq Ready mix for quantitative PCR (Sigma). The PR drop was surrounded by five water drops (first and last dummy drops not shown). The primer concentration in the common well was 50 nM. Raw data, acquired about every 150 ms from the photomultiplier are presented here. Blacks and first and second dashed lines: average, mean deviation and 95% confidence interval, respectively, of blank droplets calculated on the raw signal.

Figure 26:
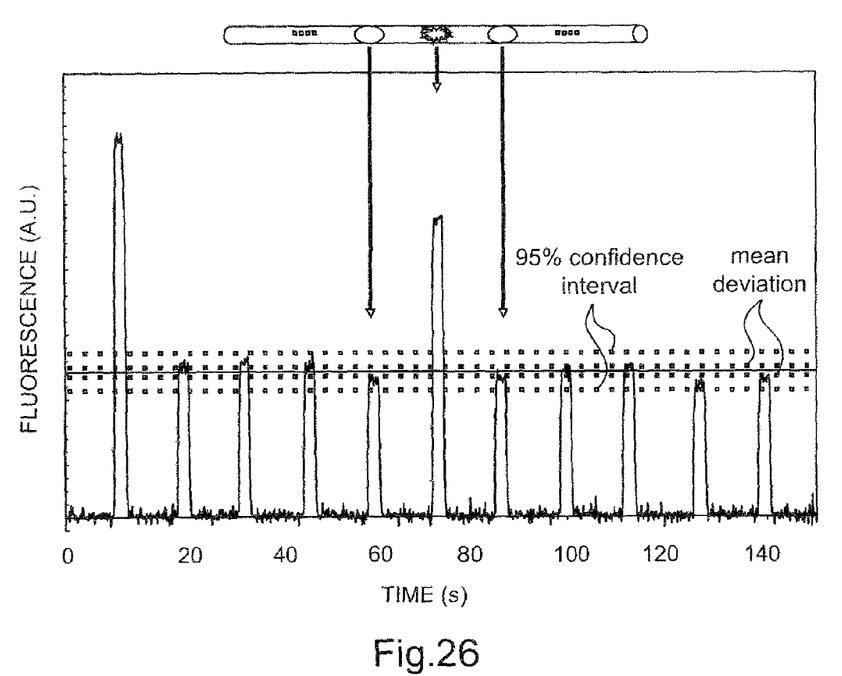

FIG. 26 shows detection of the reference gene RPLPO coding for the human acidic ribosomal phosphoprotein P0 (middle drop), surrounded by 4 drops without template. The original template DNA in the sample well is a 12.5-fold dilution from material extracted from a cancer cell line T47d by total RNA extraction followed by reverse transcription from a 50 ng/µL total RNA solution. The common well contains routine Curie hospital mix for quantitative PCR (qPCR Core Reagent Kit, Eurogentec). Black line: Raw signal acquired every 150 ms on average. Black horizontal line, dashed lines represent the signal average over control peaks, the mean deviation and 95% confidence interval calculated on raw data, respectively.

Throughout the specification and claims, "comprise a" should be understood as "comprise at least one", unless the contrary is specified. "Fluid" and "liquid", for example liquid, should be considered synonymous, as well as "droplet" and "microdroplet". A "fluid element" can be either a droplet, or a fluid spacer separating two droplets.

The invention claimed is:

1. A method for manipulating at least one flowable material with a microsampler head having at least one flowable material inlet, said method comprising:
    a) providing at least a first well with at least a first layer of a first flowable material and a second layer of a second flowable material immiscible with the first flowable material, located over said first layer, said second flowable material being a liquid, and providing at least a second well with at least a first layer of a first flowable material different from the first flowable material of said first well,
    b) locating the at least one flowable material inlet of the microsampler head within the first layer of the first well,
    c) sampling into the microsampler head a first volume of the first flowable material of the first well,
    d) displacing the at least one flowable material inlet relative to the first well to locate the at least one flowable material inlet within the second layer,
    e) sampling into the microsampler head a second volume of the second flowable material,
    f) displacing the at least one flowable material inlet relative to the first and second wells to locate the at least one flowable material inlet within the first layer of the second well, and
    g) sampling into the microsampler head a third volume of the first flowable material of the second well or dispensing into said second well a third volume of the first flowable material,
    wherein the first layer of the first flowable material in the first well has an upper surface,
    wherein the second layer of the second flowable material in the first well covers an entirety of the upper surface of the first layer of the first well, and
    wherein substantially the whole volume of the first layer of the first well is separated from air located vertically above it by a liquid material.

2. A method according to claim 1, wherein the first well is further provided with a third layer of a third flowable material located over the second layer and immiscible with the second flowable material.

3. A method according to claim 2, comprising displacing the at least one flowable material inlet relative to the first well after sampling the second volume of the second flowable material to move the at least one flowable material inlet from the second layer into the third layer of the first well.

4. A method according to claim 1, wherein the second well has over the first flowable material a second layer of a second flowable material immiscible with the first layer flowable material.

5. A method according to claim 4, wherein the second layers of the first and second wells are not in flowable material communication.

6. A method according to claim 4, comprising after sampling into the microsampler head the third volume of the first flowable material of the second well:
    h) displacing the at least one flowable material inlet relative to the second well to locate the at least one flowable material inlet within the second layer of the second well,
    i) sampling into the microsampler head a fourth volume of the second flowable material.

7. A method according to claim 6, wherein sampling at step h and sampling at step c are performed by identical or different ways selected among the active sampling and the passive sampling.

8. A method according to claim 4, wherein the second well comprises a third layer of a third flowable material immiscible with the second layer of flowable material.

9. A method according to claim 8, wherein the third layers of the first and second wells are in flowable material communication and consist of the same flowable material.

10. A method according to claim 9, comprising displacing laterally the at least one flowable material inlet within the third layer from over the first well to over the second well.

11. A method according to claim 4, wherein the second layer flowable material of the first and second wells comprise a same flowable material.

12. A method according to claim 2, wherein the third flowable material is less dense than the second flowable material.

13. A method according to claim 1, wherein the first flowable material of the first well comprises water.

14. A method according to claim 13, wherein the second flowable material of the first well comprises an organic solvent.

15. A method according to claim 2, wherein the third liquid of the first well comprises water.

16. A method according to claim 1, wherein the first flowable material of the first well comprises an organic solvent.

17. A method according to claim 16, wherein the second flowable material of the first well comprises water or a fluorinated liquid.

18. A method according to claim 2, wherein the third liquid comprises an organic solvent.

19. A method according to claim 1, wherein the first flowable material is less dense than the second flowable material.

20. A method according to claim 1, wherein the first flowable material of the first well comprises water and the first well comprises a first portion having an hydrophilic surface in contact with the first layer of the first flowable material.

21. A method according to claim 20, wherein the first well comprises a second portion having a hydrophobic surface.

22. A method according to claim 2, wherein the third flowable material is continuously renewed.

23. A method according to claim 1, wherein sampling is performed from more than 10 different wells.

24. A method according to claim 1, further comprising coalescing primary droplets of flowable material originating from the first and second wells.

25. A method according to claim 24, wherein the microsampler head comprises a first microchannel portion having a first cross-sectional area and a second microchannel portion having a second cross-sectional area larger that the first cross-sectional area, and wherein the coalescing occurs when entering the second microchannel portion.

26. A method according to claim 25, wherein the first microchannel portion is defined by a first duct force fitted into a second duct defining the second microchannel portion.

27. A method according to claim 25, wherein the at least one flowable material inlet is defined by a lower end of the first microchannel portion.

28. A method according to claim 1, wherein sampling at step c comprises creating a depression within the at least one flowable material inlet, as compared with the pressure at the top of said first layer.

29. A method according to claim 1, comprising sampling into the microsampler head a third volume of the first flowable material of the second well.

30. A method according to claim 1, comprising dispensing into the second well a third volume of the first flowable material.

31. A method according to claim 1, wherein the flowable material is a liquid.

32. A method for sampling a multiplicity of samples from a multiplicity of containers, comprising performing the method of claim 1.

33. A method for aliquoting at least one sample contained in a first container into a multiplicity of subsamples delivered to a multiplicity of second containers, comprising performing the method as defined in claim 1.

34. A method according to claim 1, whereas at least one element of a first flowable material with a volume less than 2 µl, is prepared as a droplet suspended in a second flowable material immiscible with said first flowable material.

35. A method for manipulating at least one flowable material with a microsampler head having at least one flowable material inlet, said method comprising:
  a) providing at least a first well with at least a first layer of a first flowable material and a second layer of a second flowable material immiscible with the first flowable material, located over said first layer, said second flowable material being a liquid, and providing at least a second well with at least a first layer of a first flowable material different from the first flowable material of said first well,
  b) locating the at least one flowable material inlet of the microsampler head within the first layer of the first well,
  c) sampling into the microsampler head a first volume of the first flowable material of the first well,
  d) displacing the at least one flowable material inlet relative to the first well to locate the at least one flowable material inlet within the second layer,
  e) sampling into the microsampler head a second volume of the second flowable material,
  f) displacing the at least one flowable material inlet relative to the first and second wells to locate the at least one flowable material inlet within the first layer of the second well, and
  g) dispensing into said second well a third volume of the first flowable material.

36. A method for manipulating at least one flowable material with a microsampler head having at least one flowable material inlet, said method comprising:
  a) providing at least a first well with at least a first layer of a first flowable material and a second layer of a second flowable material immiscible with the first flowable material, located over said first layer, said second flowable material being a liquid, and providing at least a second well with at least a first layer of a first flowable material different from the first flowable material of said first well,
  b) locating the at least one flowable material inlet of the microsampler head within the first layer of the first well,
  c) sampling into the microsampler head a first volume of the first flowable material of the first well,
  d) displacing the at least one flowable material inlet relative to the first well to locate the at least one flowable material inlet within the second layer,
  e) sampling into the microsampler head a second volume of the second flowable material,
  f) displacing the at least one flowable material inlet relative to the first and second wells to locate the at least one flowable material inlet within the first layer of the second well, and
  g) sampling into the microsampler head a third volume of the first flowable material of the second well or dispensing into said second well a third volume of the first flowable material,
  wherein the first layer of the first flowable material in the first well has an upper surface,
  wherein the second layer of the second flowable material in the first well covers an entirety of the upper surface of the first layer of the first well,
  wherein the first well is further provided with a third layer of a third flowable material located over the second layer and immiscible with the second flowable material, and
  wherein said third flowable material is a water-based solution.

* * * * *